US00PP36691P2

(12) United States Plant Patent
Lopez

(10) Patent No.: US PP36,691 P2
(45) Date of Patent: May 20, 2025

(54) ***BUXUS* PLANT NAMED 'WINTER ROCKET'**

(50) Latin Name: *Buxus microphylla*
Varietal Denomination: WINTER ROCKET

(71) Applicant: Flat Rock Nursery, Wrightsville, GA (US)

(72) Inventor: Juan Lopez, Wrightsville, GA (US)

(73) Assignee: Flat Rock Nursery, Wrightsville, GA (US)

( * ) Notice: Subject to any disclaimer, the term of this patent is extended or adjusted under 35 U.S.C. 154(b) by 0 days.

(21) Appl. No.: 18/762,289

(22) Filed: Jul. 2, 2024

(51) Int. Cl.
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct cultivar of *Buxus* plant named 'WINTER ROCKET' is disclosed, characterized by a compact, upright plant habit and glossy dark green foliage. Plants have shown deer resistance as well as resistance to the normal diseases and pests of Boxwood. Plants have also been observed drought tolerant and heat tolerant to 110-degree F. without negative effects. The new cultivar is a *Buxus*, suitable for ornamental garden purposes.

1 Drawing Sheet

Latin name of the genus and species: *Buxus microphylla*.
Cultivar denomination: 'WINTER ROCKET'.

BACKGROUND OF THE INVENTION

The new cultivar, hereinafter referred to as 'WINTER ROCKET', was discovered at a nursery in Wrightsville, GA. The interesting new cultivar was discovered as a branch mutation on a plant of the parent variety, the unpatented *Buxus microphylla* 'Wintergreen' in June of 2019. This discovery was made in an area of containers of all 'Wintergreen' plants.

After identifying the new cultivar as a potentially interesting selection, the inventor first organized asexual propagation of 'WINTER ROCKET' in July of 2019, using semi-softwood cuttings at the same nursery in Wrightsville, GA. The inventor continued controlled testing and propagation, assessing stability of the unique characteristics of this cultivar. At least three generations have been reproduced and have shown that the unique features of this cultivar are stable and reproduced true to type.

SUMMARY OF THE INVENTION

The cultivar 'WINTER ROCKET' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WINTER ROCKET' These characteristics in combination distinguish 'WINTER ROCKET' as a new and distinct *Buxus* cultivar:

1. Tight and compact growth.
2. Upright habit.
3. Deer resistance.

4. Pest and disease resistance.
5. Heat and drought tolerance.

COMPARISON TO PARENT CULTIVAR

'WINTER ROCKET' is similar in most horticultural characteristics to the parent variety. Plants of the new cultivar 'WINTER ROCKET' however, differ in the following:

1. Foliage of the new cultivar is darker green than foliage of the parent variety.
2. Stems of the new cultivar are stronger than stems of the parent variety.
3. Growth habit of the new cultivar is more upright than growth habit of the parent variety.
4. The new cultivar is resistant to boxwood blight (*Calonectria pseudonaviculata*); the parent variety is susceptible.
5. The new cultivar grows faster and is ready for sales sooner than the parent variety.

COMMERCIAL COMPARISON

'WINTER ROCKET' is similar in most horticultural characteristics to the unpatented commercial cultivar *Buxus* 'Winter Gem'. Plants of the new cultivar 'WINTER ROCKET' however, differ in the following:

1. Foliage of the new cultivar darker green than foliage of 'Winter Gem'.
2. Plants of the new cultivar are more upright and dense than plants of this comparator.
3. Mature size of the new cultivar is smaller than the mature size of this comparator.
4. Stems of the new cultivar are stronger than stems of this comparator.
5. The new cultivar shows more resistance to pests and diseases compared to 'Winter Gem'.

'WINTER ROCKET' is similar in most horticultural characteristics to the unpatented commercial cultivar *Buxus*

'Green Velvet'. Plants of the new cultivar 'WINTER ROCKET' however, differ in the following:

1. Foliage of the new cultivar darker green than foliage of 'Green Velvet'.
2. Plant shape of the new cultivar is upright; plant shape of this comparator is round.
3. Plants of the new cultivar grow more rapidly than plants of this comparator.
4. Stems of the new cultivar are stronger than stems of this comparator.
5. The new cultivar shows more resistance to pests and diseases compared to 'Green Velvet'.

BRIEF DESCRIPTION OF THE PHOTOGRAPH

The accompanying photograph 1 illustrates in full color a typical plant of 'WINTER ROCKET' grown outdoors in Camarillo, CA. The plant is approximately 1.5 years old. The plant photographed has not been pruned and naturally grows as pictured. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'WINTER ROCKET' plants grown in outdoors in Camarillo, CA. Plants are approximately 1 to 2 years old, in a 2-gallon nursery container. Measurements and numerical values represent averages of typical plant types.

Botanical classification: *Buxus microphylla* 'WINTER ROCKET'.

PROPAGATION

Time to rooting: 30 days in summer, 45 days in winter at 18° C. to 27° C.

Root description: Moderately dense, moderately free branching, fleshy, medium thickness. Light brown to tan in color, not accurately measured with R.H.S. chart.

PLANT

Growth habit: Upright and compact.
Plant shape: Broad columnar.
Height: 35 cm.
Plant spread: 22 cm.
Growth rate: Rapid. Plants finish in a 1-gallon pot at 16 to 18 inches tall from a rooted cutting within 1 year.
Vigor: Vigorous. Approximately 50% faster growing than the parent variety in a commercial situation.
Branching characteristics: Basal; some pinching required to encourage abundant branching.
Quantity of branches: 3 to 6 main branches. Lateral branches occurring 2 to 5 cm along main branches.
Main branch internode length: 2.0 cm to 4.5 cm.
Length of main branches: 15 to 30 cm.
Diameter of lateral branches: 4 mm.
Length of lateral branches: 8 to 19 cm.
Diameter of lateral branches: 3 mm.

Branch descriptors, main and lateral branches:
*Shape*.—Rounded.
*Aspect*.—Straight.
*Angle*.—15° to 25° from center of plant.
*Color*.—Immature: RHS Green 143C. Mature: RHS Grey-Brown 199A with scales Greyed-Green 198D.
*Strength*.—Strong and moderately flexible.
*Texture*.—Immature: glabrous; Mature: scaly.

FOLIAGE

Leaf:
*Arrangement*.—Opposite, single.
*Shape of blade*.—Very broad elliptic to globose.
*Length*.—Average 2 cm.
*Width*.—Average 1.4 cm.
*Apex*.—Blunt rounded.
*Base*.—Broadly tapered.
*Attachment*.—Petiolate.
*Margin*.—Entire.
*Texture of top surface*.—Glabrous with a slightly waxy cuticle.
*Texture of bottom surface*.—Glabrous.
*Appearance of top surface*.—Shiny.
*Appearance of bottom surface*.—Matte.
*Color*.—Young foliage upper side: RHS Green 137A with a sheen of 143A. Young foliage under side: RHS Green 143C. Mature foliage upper side: RHS Green 139A. Mature foliage under side: RHS Green 143A.
*Venation*.—Type: Pinnate. Venation Color: Upper: Center vein Yellow-Green 145A. Lateral veins indistinguishable from leaf blade. Lower: Center vein Green 143C. Lateral veins indistinguishable from leaf blade.

Petiole:
*Length*.—Average 2 mm.
*Diameter*.—2 mm.
*Texture, upper side*.—Glabrous.
*Texture, under side*.—Glabrous.
*Color, upper side*.—RHS Yellow-Green 145A.
*Color, under side*.—RHS Green 143C.

FLOWER

Not observed to date.

REPRODUCTIVE ORGANS

Not observed to date.

OTHER CHARACTERISTICS

Fruit and seeds: Not observed.
Disease and pest resistance: Resistance to *Calonectria pseudonaviculata* has been observed. Resistance to pests of *Buxus* also observed.
High temperature tolerance: Observed to tolerate 110° F. without negative effects.
Drought tolerance: Observed to tolerate drought conditions.

What is claimed is:

1. A new and distinct cultivar of *Buxus* plant named 'Winter Rocket' as herein illustrated and described.

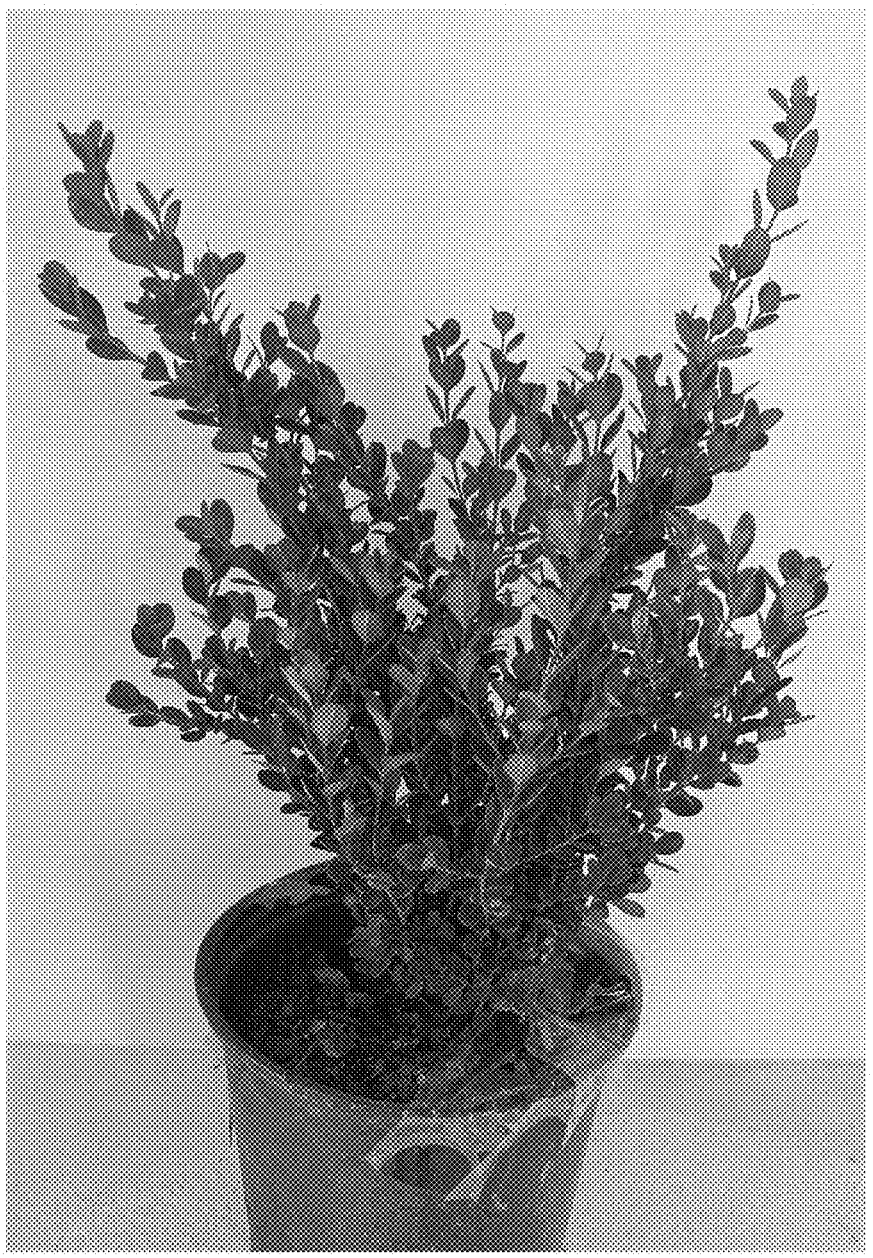

* * * * *